United States Patent
Lokken et al.

(10) Patent No.: US 11,524,040 B2
(45) Date of Patent: Dec. 13, 2022

(54) COMPOSITION FOR THE TREATMENT OF ACNE

(71) Applicant: Charlotte's Web, Inc., Boulder, CO (US)

(72) Inventors: Jeffrey Lokken, Buffalo, NY (US); Katherine Cwiklinski, Buffalo, NY (US)

(73) Assignee: Charlotte's Web, Inc., Boulder, CO (US)

( * ) Notice: Subject to any disclaimer, the term of this patent is extended or adjusted under 35 U.S.C. 154(b) by 0 days.

(21) Appl. No.: 17/409,963

(22) Filed: Aug. 24, 2021

(65) Prior Publication Data

US 2022/0054567 A1 Feb. 24, 2022

Related U.S. Application Data

(60) Provisional application No. 63/069,180, filed on Aug. 24, 2020.

(51) Int. Cl.
| | |
|---|---|
| *A61K 36/15* | (2006.01) |
| *A61P 17/10* | (2006.01) |
| *A61K 31/015* | (2006.01) |
| *A61K 31/045* | (2006.01) |
| *A61K 31/60* | (2006.01) |

(Continued)

(52) U.S. Cl.
CPC .............. *A61K 36/15* (2013.01); *A61K 9/06* (2013.01); *A61K 31/015* (2013.01); *A61K 31/045* (2013.01); *A61K 31/05* (2013.01); *A61K 31/355* (2013.01); *A61K 31/375* (2013.01); *A61K 31/4166* (2013.01); *A61K 31/60* (2013.01); *A61K 36/185* (2013.01); *A61K 36/28* (2013.01); *A61K 36/286* (2013.01); *A61K 36/30* (2013.01); *A61K 36/53* (2013.01); *A61K 36/71* (2013.01); *A61P 17/10* (2018.01)

(58) Field of Classification Search
None
See application file for complete search history.

(56) References Cited

U.S. PATENT DOCUMENTS

| | | |
|---|---|---|
| 6,780,825 B2 | 8/2004 | Piterski et al. |
| 7,350,256 B2 | 4/2008 | Benjamin et al. |

(Continued)

FOREIGN PATENT DOCUMENTS

| | | |
|---|---|---|
| CA | 3017698 A1 | 10/2017 |
| CA | 3042487 A1 * | 5/2018 |

(Continued)

*Primary Examiner* — Michael V Meller
(74) *Attorney, Agent, or Firm* — Stadler IP Law PLLC

(57) ABSTRACT

A composition for the treatment of acne. The composition works without drying out the skin and exacerbating the cycle of acne, while promoting healing and reducing inflammation. The composition includes a cannabidiol, terpenoids, an antimicrobial, a soothing agent, a healing agent, or an anti-inflammatory agent, a healthy skin promoter, an antioxidant, and a mild, naturally derived antimicrobial agent. The composition may also include emulsifiers, humectants, preservatives, chelating agents, stabilizers, colorants, and fragrances. The composition may also include oils and fatty acids such as medium chain triglycerides (caprylic/capric triglyceride), *Cannabis Sativa* (hemp seed) oil, and *Nigella Sativa* (black cumin) seed oil.

1 Claim, 8 Drawing Sheets

| | OTC | NB | AP 1 | AP 2 |
|---|---|---|---|---|
| Avg. % Change | 7% | 12% | -2% | -17% |

(51) Int. Cl.

| | |
|---|---|
| A61K 31/05 | (2006.01) |
| A61K 31/375 | (2006.01) |
| A61K 31/355 | (2006.01) |
| A61K 36/53 | (2006.01) |
| A61K 31/4166 | (2006.01) |
| A61K 36/30 | (2006.01) |
| A61K 36/28 | (2006.01) |
| A61K 36/286 | (2006.01) |
| A61K 36/71 | (2006.01) |
| A61K 9/06 | (2006.01) |
| A61K 36/185 | (2006.01) |

(56) References Cited

U.S. PATENT DOCUMENTS

| | | | |
|---|---|---|---|
| 8,758,826 | B2 | 6/2014 | Bevier |
| 9,956,151 | B2 | 5/2018 | Santhanam et al. |
| 10,226,496 | B2 | 3/2019 | Sekura |
| 10,493,018 | B1 | 12/2019 | Lincoln |
| 10,603,344 | B2 | 3/2020 | Letzel et al. |
| 10,653,778 | B2 | 5/2020 | Bannister et al. |
| 10,738,268 | B2 | 8/2020 | Leo |
| 10,864,189 | B2 | 12/2020 | Borok |
| 10,933,008 | B1 | 3/2021 | Arkles et al. |
| 10,945,952 | B2 | 3/2021 | Kelm et al. |
| 10,966,953 | B2 | 4/2021 | Koren |
| 2007/0166255 | A1 | 7/2007 | Gupta |
| 2015/0374595 | A1 | 12/2015 | Albrecht |
| 2016/0235661 | A1 | 8/2016 | Changoer et al. |
| 2016/0250270 | A1 | 9/2016 | Wendschuh et al. |
| 2016/0367676 | A1 | 12/2016 | Burnam |
| 2017/0042791 | A1 | 2/2017 | Ghalili et al. |
| 2018/0021247 | A1 | 1/2018 | Ghalili et al. |
| 2018/0344786 | A1 | 12/2018 | Thacker, Jr. et al. |
| 2019/0060220 | A1 | 2/2019 | Postrel |
| 2019/0224137 | A1 | 7/2019 | Callahan |
| 2019/0269747 | A1 | 9/2019 | Bomstein et al. |
| 2019/0321306 | A1 | 10/2019 | Vu et al. |

FOREIGN PATENT DOCUMENTS

| | | |
|---|---|---|
| WO | WO2013142471 A3 | 9/2013 |
| WO | WO2014081715 A1 | 5/2014 |
| WO | WO2018087766 A1 | 5/2018 |
| WO | WO2018185230 A1 | 10/2018 |

* cited by examiner

| Time | Untreated | OTC | % Increase from OTC | % Decrease from Untreated |
|---|---|---|---|---|
| 0 hr | 274 | 274 | 0% | 0% |
| 1 hr | 354 | 208 | 70% | 41% |
| 2 hr | 325 | 183 | 78% | 44% |
| 3 hr | 312 | 191 | 63% | 39% |
| 4 hr | 334 | 254 | 32% | 24% |
| 5 hr | 338 | 231 | 46% | 32% |
| Average Percent Change | | | 58% | 36% |

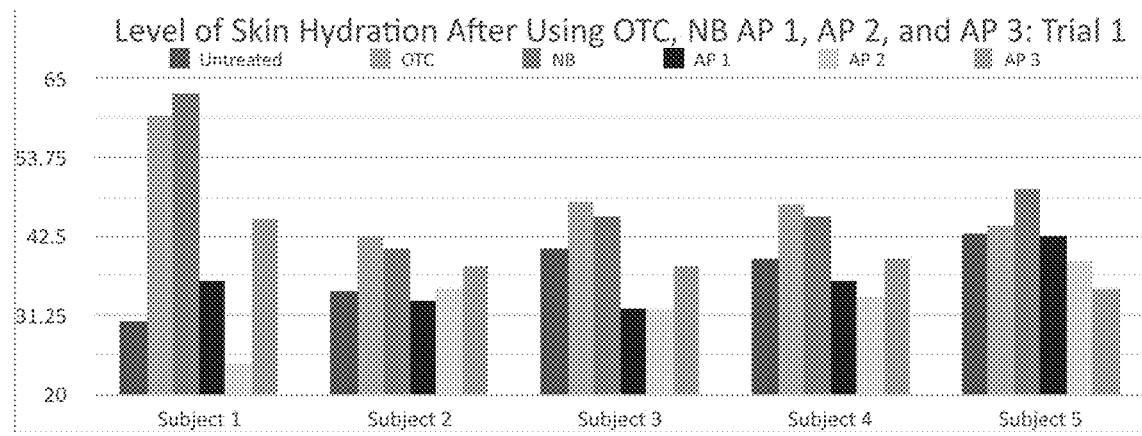
FIG. 12
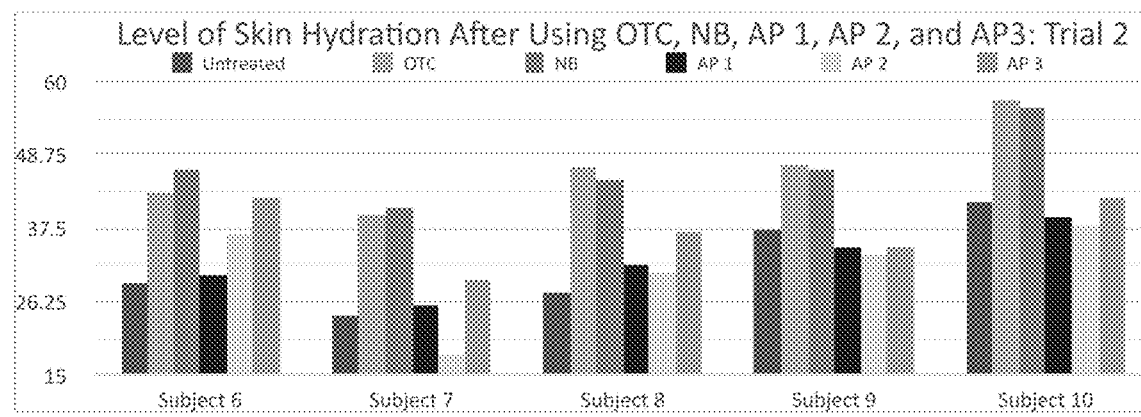
FIG. 13
| Product | OTC | NB | AP 1 | AP 2 | AP 3 |
|---|---|---|---|---|---|
| Average % Change | 39.70% | 41.50% | 17% | -7% | 12.60% |
FIG. 14

|  | OTC | NB | AP 1 | AP 2 |
|---|---|---|---|---|
| Avg. % Change | 7% | 12% | -2% | -17% |

COMPOSITION FOR THE TREATMENT OF ACNE

CROSS-REFERENCE TO RELATED APPLICATIONS

This application is a Nonprovisional application of pending U.S. Provisional Application No. 63/069,180, filed Aug. 24, 2020, the disclosure of which is incorporated herein by reference.

FIELD OF INVENTION

This invention is directed to a composition for treating acne. More particularly, the composition works without drying out the skin and exacerbating the cycle of acne, while promoting healing and reducing inflammation.

BACKGROUND OF INVENTION

Acne, which is also known as acne vulgaris, is a long-term skin disease that occurs when hair follicles are clogged with dead skin cells and oil from the skin. It is characterized by blackheads or whiteheads, pimples, blemishes, oily skin, and possible scarring. It primarily affects areas of the skin with a relatively high number of oil glands, including the face, upper part of the chest, and back. The resulting appearance can lead to anxiety, reduced self-esteem, and in extreme cases, depression or thoughts of suicide.

"The causes leading to acne are a higher than normal amount of sebum production, excessive keratin deposition, colonization of the follicle by bacteria (*Propionibacterium acnes*) and the local release of pro-inflammatory chemicals in the skin. There is a strong genetic component in acne development shown by twin and familial studies. Diet and microbiome irregularities are also important factors in the development of this disease. It is normal for adolescents to develop a surge of acne during puberty, caused by the higher sex hormone levels, such as testosterone and estrogen." https://gregorzorn.com/medical-conditions/acne/

The most prevalent traditional topical products fall into two categories, 1.) oxidizers such as benzoyl peroxide and 2.) acids such as salicylic acid. These ingredients are both monographed ingredients as outlined by the United States Food and Drug Administration. There are many challenges with the use of these products, particularly as they are most often the sole drivers in formulas. The use of such products puts the skin in imbalance, and causes skin irritation that can further exacerbate acne creation, acne lesions and hyperpigmentation spots. One such problem is the drying out of the skin and its naturally produced sebum (oil). The human body's reaction to such a condition is to overproduce oil and to increase skin proliferation and henceforth the repeated acne cycle continues. Another such problem is the drastic reduction of not only acne causing bacteria, but many of the good bacteria that create a proper skin balance are killed in the process with the use of such traditional products. This creates an 'open playing field' on the skin for further propagation of negative, acne causing bacteria and henceforth furthering the acne cycle. Other treatments for acne include antibiotics, which may run the risk of developing resistant bacteria and have no capability of neutralizing the secretory toxins of bacteria.

Therefore, there is a need for an acne/blemish topical product that is free of or has a reduced level of these common acids and oxidizing agents. There is also a consumer demand for products that are plant-derived, from natural sources and that include ingredients that have undergone less processing and have no to minimal alterations from their native chemical state and composition.

SUMMARY OF THE INVENTION

Accordingly, it is the subject of this invention to provide a composition for the treatment of acne that is free of acids and oxidizing agents or has a reduced level of acids and oxidizing agents as compared to those currently on the market.

The composition of the present disclosure provides a unique, holistic, balanced approach to treating acne in the following ways:

instead of drying out the skin, the instant composition creates a lipostatic balance in the sebocytes of the skin, which aids in minimizing acne;

the instant composition restores balance to the proliferation of skin cell turnover, instead of causing hyperproliferation like other anti-acne products currently available on the market, the composition of the present disclosure restores balance of skin cell turnover;

the instant composition soothes the skin, reduces inflammation, and speeds up the healing process through use of antioxidants and collagen building ingredients (cellular inflammation can exacerbate acne conditions and delay the healing of acne-induced hyperpigmentation spots and these spots often last many days or even weeks while the lesion is healing due to cellular inflammation as it relates to inflammatory cytokines tested (interferon gamma reactive oxygen species, tumor necrosis factor alpha, interleukin 6), and the duration of such spots can greatly increase anxiety and reduce self-esteem);

the instant composition provides mild anti-bacterial balancing effects through the use of terpenoids found in full spectrum hemp extract containing Cannabidiol (CBD), other cannabinoids, terpenoids, flavonoids and others; and most ingredients used will be natural, naturally derived and/or non-animal sourced.

BRIEF DESCRIPTION OF THE DRAWINGS

FIG. 12 depicts skin hydration results.

FIG. 13 depicts skin hydration results.

FIG. 14 skin hydration results.

DETAILED DESCRIPTION OF THE INVENTION

Figure 1:
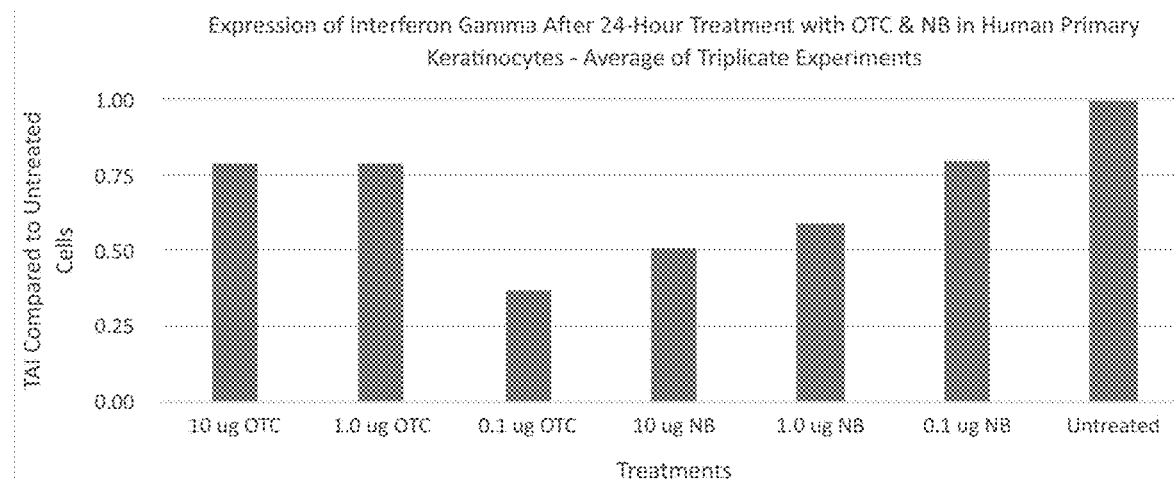
FIG. 1 depicts a table comparing Interferon Gamma expression results.

The term "water-based moisture mix" as used herein and in the appended claims includes the composition commercially known as natural moisturizing factors. The composition includes water, sodium PCA, panthenol, glycerine, sodium hyaluronate, proline, and hydroxyproline.

The term "salicylic acid mix" as used herein and in the appended claims includes salicylic acid, polydextrose, dextrin, amylopectin, and niacinamide.

The term "rosemary extract mix" as used herein and in the appended claims includes ascorbyl palmitate, mixed tocopherols, and rosemary extract.

The term "CB2 receptor binding agent" refers to any compound that activates or binds to the cannabinoid receptor type 2. It is noted that CB2 receptor binding agents may be derived naturally or synthetically. This includes, but is not limited to, extracts from the *Cannabis sativa* plant, full spectrum cannabidiol (hemp extract), full spectrum cannabigerol (hemp extract), cannabidiol broad spectrum, cannabigerol broad spectrum, cannabidiol isolate, cannabigerol isolate, and any synthetically derived cannabinoid analogues.

In one embodiment, the composition is comprised of: a cannabinoid or any other CB2 receptor binding agent; added terpenoid(s); an antimicrobial; a soothing agent, a healing agent, or an anti-inflammatory agent; a healthy skin promoter; an antioxidant such as vitamin E; and a mild, naturally derived antimicrobial agent.

The composition further comprises: emulsifiers; humectants; preservatives; chelating agents; stabilizers; colorants; and fragrances.

The composition further comprises: oils and fatty acids such as medium chain triglycerides (caprylic/capric triglyceride), *Cannabis sativa* (hemp) seed oil, ethyl linoleate, and *Nigella sativa* (black cumin) seed oil.

In one embodiment, the cannabidiol has a level of tetrahydrocannabinol (THC) that is less than 0.3%. In other embodiments, the level of THC may be higher or may not be present. The cannabidiol may be a concentrated, isolate, of or in a full hemp extract that contains various cannabinoids, terpenoids, and flavonoids.

In one embodiment, the terpenoid is a *cannabis* hemp plant terpenoid.

In one embodiment, the antimicrobial is cannabigerol.

In one embodiment, the anti-inflammatory is comfrey extract and in still further embodiments, the anti-inflammatory is allantoin or rosemarinic acid or CBD or other cannabinoids or combinations thereof.

In one embodiment, the healthy skin promoter is a stable vitamin C-derivative such as ascorbyl palmitate, magnesium ascorbyl palmitate, or sodium ascorbyl phosphate.

In another embodiment, the soothing agent, or healing agent, or anti-inflammatory ingredient may be bisabolol, ascorbic acid (vitamin C) and its derivatives such as ascorbyl palmitate, sodium ascorbyl phosphate, tetrahexyldecyl ascorbate, 3-glyceryl ascorbate, magnesium ascorbyl phosphate, ascorbyl tetraisopalmitate, ethyl ascorbic acid, ascorbyl glucoside, aminopropyl ascorbyl phosphate, myristyl 3-glyceryl ascorbate, allantoin (including plant extracts that are high in allantoin such as comfrey, sugar beets, chamomile, and wheat sprouts), vitamin E and its derivatives such as tocopheryl acetate, mixed tocopherols, gamma tocopherol, alpha tocopherol, tocopheryl, tocopheryl succinate linoleate, tocopheryl nicotinate and sodium tocopheryl phosphate, terpenoids and terpenoids such as limonene, myrcene, linalool, caryophyllene, alpha-bisabolol, delta-3-carene, eucalyptol, nerolidol and pinene among others. It is believed that these components will help with the reduction of hyper-pigmentation spots as a function of size, redness, and duration.

In another embodiment, the mild antimicrobial agent is natural spruce resin, which is sold under the Trade name Resol G™ or Resol™ Skincare and can be obtained through the Finnish Company Repolar. In a preferred embodiment, the antimicrobial is natural and may be terpenes or terpenoids, including, but not limited to myrcene, terpinolene, terpineol, alpha-bisabolol, alpha-humulene, alpha-pinene, beta-pinene, beta-caryophyllene, (+)-limonene, eucalyptol, thymol, borneol, nerolidol, gerianol, menthol, citronellol, carveol, eugenol, linalyl acetate, linalool, and zingiberene. Preferably, the natural antimicrobial ingredient is neither an oxidizer (such as the over the counter monographed ingredient benzoyl peroxide), an acid (pH below 4.0, more particularly not an alpha or beta hydroxy acid), nor an alcohol (such as isopropyl alcohol).

In one embodiment, the composition further comprises a minimal amount of salicylic acid or encapsulated salicylic acid, while in another embodiment, the composition is a natural-based formulation that uses natural spruce resin.

In a preferred embodiment, the cannabidiol used is a full spectrum hemp extract containing cannabidiol that may or may not have a level of THC<0.3%. This ingredient has the benefits of being:

lipostatic: anti-proliferative; anti-inflammatory; and mildly antibacterial.

The composition of the present disclosure may be delivered topically as a liquid, a spray, a serum, an ointment, a lotion, or a cream.

Also, without intending to be bound by theory, it is believed that full spectrum hemp extract containing cannabidiol is lipostatic through at least four different pathways. It is also believed to be anti-proliferative through at least four different pathways, and anti-inflammatory through at least three different pathways.

Cannabinoids are lipostatic through the ARHGAP9 pathway, interference with the MAPK pathway, downregulates NRIP1 and may work on the mTOR Pathway.

Cannabinoids are anti-proliferative through the MKI67 pathway, TRPV4-dependent interference with the MAPK pathway, TRPV4-dependent cell cycle-arrest and possibly, the mTOR pathway.

Cannabinoids are anti-inflammatory and anti-pathogenic by upregulating the TRIB3 gene, inhibition of the p65-NF-kB-Pathway and upregulation of the LL-37 cathelicidin.

Hemp and safflower oil contain amounts of high linoleic acid. One hypothesis suggests that a deficiency of linoleic acid may lead to a deficit in 5α-reductase type 1 and may be associated with abnormal hyper-keratinization, leading to microcomedones being formed that are associated with acne lesions.

Also without intending to be bound by theory, the stable vitamin C-derivative provides antioxidant and collagen building properties, while vitamin E provides antioxidant properties and healing of acne lesions and scars.

The composition of the present disclosure is a unique, holistic, balanced approach to treating acne in the following ways to be described presently.

Instead of drying out the skin, the composition creates a lipostatic balance in the sebocytes, thereby providing a proper balance of natural skin oils that will aid in minimizing acne. Traditionally, it has been thought that anti-acne treatments must be oil free and drying so as to not clog the pores. In fact, currently available anti-acne treatments on the market advertise that they are oil free and in many cases, they also advertise that they are drying. The composition of the present disclosure undermines the premise that anti-acne treatments must be oil free and drying. Rather, the composition of the present disclosure includes oils so as to be moisturizing and not drying. Surprisingly, the added oils and moisturization actually aids the composition's ability to effectively treat acne.

The composition disclosed herein restores balance to the proliferation of skin cell manufacture instead of drying out the skin and causing hyperproliferation as seen with traditional anti-acne products.

Inflammation can exacerbate acne conditions and delay the healing of acne-induced hyperpigmentation spots. These spots often last many days or even weeks while the lesion is healing, and the duration of such spots can greatly increase anxiety and reduce self-esteem. The composition disclosed herein soothes skin and reduces inflammation. It also speeds up the healing process through use of antioxidants and collagen building ingredients, thus the healing of acne-induced hyperpigmentation spots will occur more quickly.

Moreover, the composition will have mild anti-bacterial balancing effects through the use of terpenoids found in full spectrum hemp extract containing, cannabidiol, other cannabinoids, terpenoids, flavonoids, and others.

To meet the increasing market for natural products, the majority of ingredients used will be natural, naturally derived and/or non-animal.

The vast majority of acne products do not contain oils and fatty acids (this is because it has been historically thought that oils and fatty acids contribute to acne). Nonetheless, it is believed that the oil of the composition disclosed herein will help maintain the balance of the skin.

Other Treatments and Side-Effects

Antibiotics for acne treatment may run a risk of developing resistant bacteria and have no capability of neutralizing the secretory toxins.

Inflammation has long been recognized as important in the pathogenesis of acne; however, until recently it was considered a secondary event. Studies over the past decade have demonstrated a central role for inflammation in the development of acne lesions and have opened new opportunities for therapeutic intervention.

Inflammatory molecules are produced and released in many cell types in the skin of acne sufferers. This inflammation can be caused indirectly by age and sex related changes in hormones, medications, diets containing certain carbohydrates, and heritable genetics. The indirect triggers lead to cellular changes that allow the skin to become susceptible to forming acne lesions and blemishes.

Androgens, a type of hormone, enlarge the sebaceous glands of the body and increase production of oily sebum in sebocytes. This is a direct cause of comedones. Comedones are the bumps that erupt into white-heads and black-heads on the surface of the skin. The medications that cause acne are typically corticosteroids, testosterone and lithium and contribute to acne in a way similar as androgens and interfere with the previously described natural hormone production. Dietary carbohydrates, particularly simple sugars, and high glycemic carbohydrates, increase the blood sugar leading to an increase of insulin which aids in comedone synthesis by causing an increase in oil production. Elevated production of oily sebum results from genetic components, hormones, certain medications, and carbohydrates. The oil and sebum on the skin create a suitable anaerobic environment for increased bacteria growth in the pores and an increase of inflammation in the surrounding cells.

Keratinocytes are a cell type that contribute to the pathogenesis of acne vulgaris by releasing proinflammatory cytokines and transcription factors to surrounding cells. Some of these cytokines and factors are interferon gamma (IFN-γ), reactive oxygen species (ROS) and interleukin-6 (IL-6). All of these play a role in the pathogenesis along the multicellular pathway of acne.

In-Vitro Data

In a study using human primary keratinocytes, two formulations were analyzed, Natural Blemish Light Lotion (NB) and Natural Blemish OTC Lotion (OTC) for unique properties. All the following experiments include a 24-hour treatment of the finished products used in the dilutions shown and were analyzed by quantitative polymerase chain reaction (qPCR).

The following nomenclature is used: the Natural Blemish OTC composition (see Example 3) is referred to as OTC, the Natural Blemish Light Lotion composition (see Example 2) is referred to as NB, and a commonly available anti-acne composition containing 10% benzoyl peroxide is referred to as AP.

Interferon Gamma (IFN-γ) is a cytokine and is one of the key factors in inflammatory skin diseases, which mediates Th-1 type inflammation and growth inhibition of keratinocytes. IFN-γ is known to exist in the epidermis in psoriasis and subcutaneous injection of IFN-γ induces psoriatic plaques in psoriasis patients (Fierlbeck et al, 1990). As seen in FIG. 1, the compositions of the present disclosure both reduce the expression of IFN-γ in every concentration tested.

Figure 2:
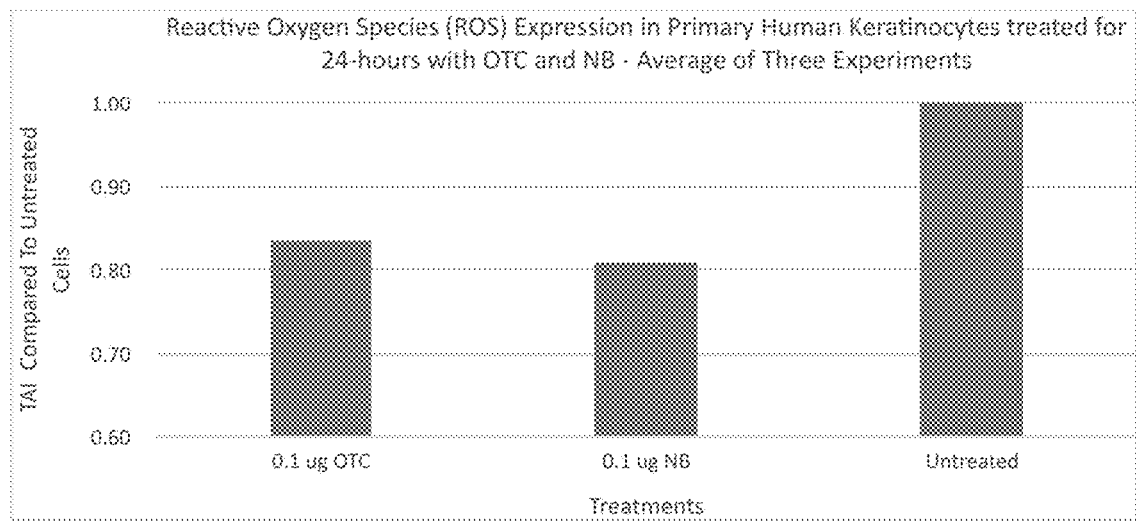
FIG. 2 depicts a table comparing Reactive Oxygen Species expression results.

Reactive oxygen species (ROS) are toxic molecules and play critical roles in many of the inflammatory skin diseases. (Oztas M O, Balk M, Ogus E, Bozkurt M, Ogus I H, Ozer N. The role of free oxygen radicals in the aetiopathogenesis of rosacea. Clin Exp Dermatol. 2003; 28(2):188-192). In acne, sebum produced by sebaceous glands, content changes and reactive oxygen species (ROS) may be released from the impacted damaged follicular walls; at the same time, it is thought that this may be the reason for the progress of the inflammation in the pathogenesis of the disease ([Briganti S, Picardo M. Antioxidant activity, lipid peroxidation and skin diseases. What's new? J Eur Acad Dermatol Venereol. 2003; 17(6):663-669. [PubMed]). Treatment with low levels of both compositions of the present disclosure reduce the expression of ROS in keratinocytes in-vitro. At a concentration of 0.1 micrograms per milliliter, both products reduced expression of ROS in Keratinocytes. The reduction was 16.0% in OTC and 19.0% in NB, as shown in FIG. 2.

Figure 3:
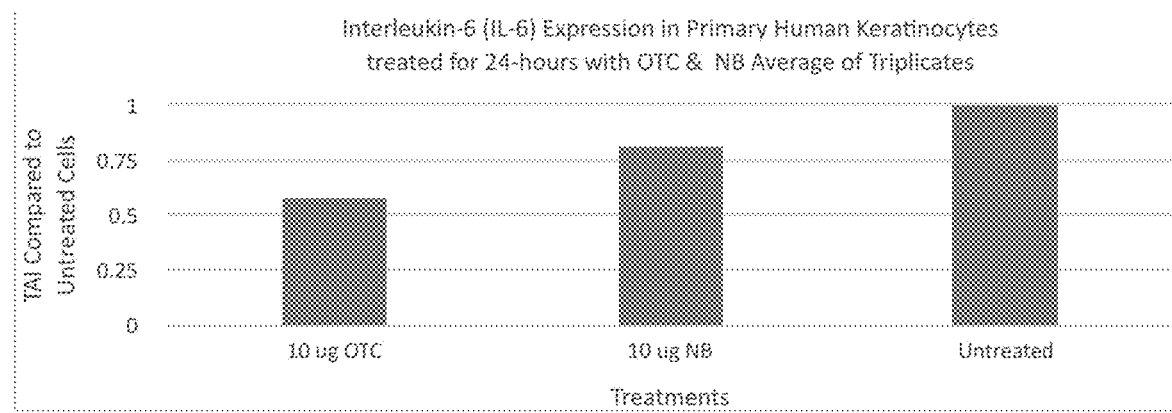
FIG. 3 depicts a table comparing Interleukin-6 expression results.

Interleukin-6 (IL-6) is a well-established marker for inflammation. Largely produced in the skin by keratinocytes, its production leads to the activation of the STAT3 pathway which has been linked to the pathogenesis of many inflammatory skin diseases (Activation of Janus kinase signaling pathway in acne lesions, Sara Mohamed Awad, Yasmin Mostafa Tawfik, Mohamed Ahmed El-Mokhtar, Amira F. El-Gazzar, Amira Ali Abdel Motaleb First published: 19 Nov. 2020 https://doi.org/10.1111/dth.14563). In addition, IL-6 exerts stimulatory effects on T-cells and B-cells, thus favoring chronic inflammatory responses. (Gabay C. Interleukin-6 and chronic inflammation. Arthritis Res Ther. 2006; 8 Suppl 2(Suppl 2):S3. doi:10.1186/ar1917). As shown in FIG. 3, the compositions of the present disclosure, OTC and NB, reduced the expression of IL-6 by 37.0% and 21.0%, respectively. CBD isolate was used as a control in the same concentration as present in the invention and showed 6.0% expression reduction, demonstrating that the compositions of the present disclosure, OTC and NB, reduce inflammation more effectively than just CBD alone. That is, the compositions work better to reduce expression of IL-6 than the individual ingredients, namely CBD alone.

Because sebum production is a major factor in the pathophysiology of acne vulgaris, experiments were performed using human primary sebocytes isolated from the eye area. The main function of sebocytes is considered to be the production of lipids to moisturize the skin. However, it recently became apparent that sebocytes release chemokines and cytokines and respond to proinflammatory stimuli as well as the presence of bacteria. (Attii M, Lovászi M, Garzorz N, Atenhan A, Quaranta M, Lauffer F, Konstantinow A, Küpper M, Zouboulis C C, Kemeny L, Eyerich K, Schmidt-Weber C B, Töröcsik D, Eyerich S. Sebocytes contribute to skin inflammation by promoting the differentiation of T helper 17 cells. Br J Dermatol. 2018 March; 178(3):722-730. doi: 10.1111/bjd.15879. Epub 2018 Jan. 9. PMID: 28799643). The overproduction of sebum, proinflammatory chemokines and cytokines released from sebocytes all contribute to the formation of comedones on the skin. Both OTC and NB were studied as well as AP to investigate the efficacy of these products.

Figure 4:
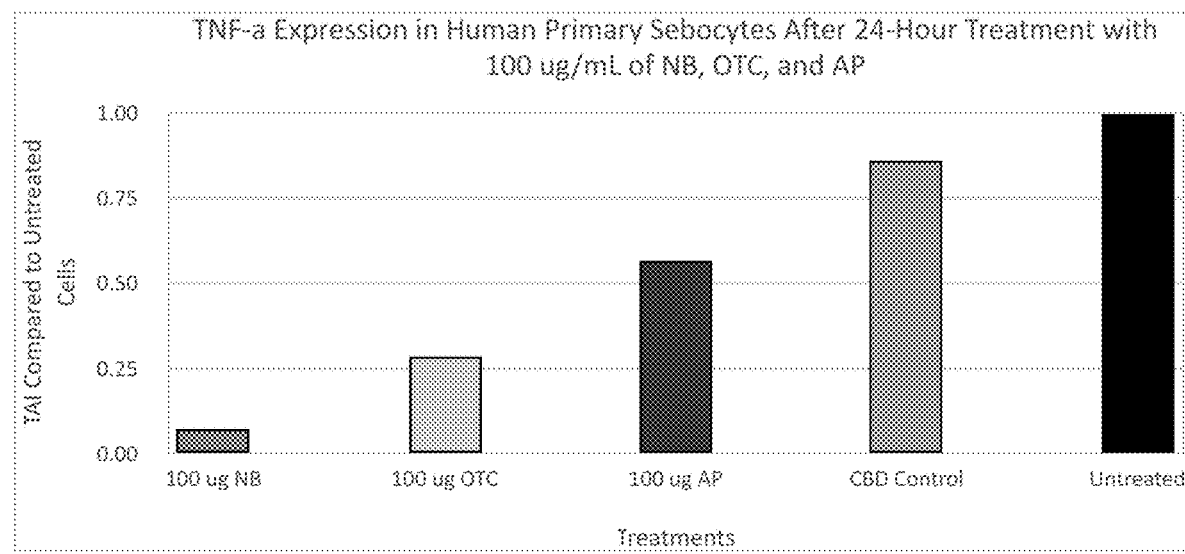
FIG. 4 depicts a table comparing TNF-a expression results.

Tumor necrosis factor (TNF-α) is a pro-inflammatory cytokine. TNF-α has been shown to play a pivotal role in orchestrating the cytokine cascade in many inflammatory diseases and because of this role as a "master-regulator" of inflammatory cytokine production, it has been proposed as a therapeutic target for a number of diseases. Parameswaran N, Patial S. Tumor necrosis factor-α signaling in macrophages (Crit Rev Eukaryot Gene Expr. 2010; 20(2):87-103. doi:10.1615/critreveukargeneexpr.v20.i2.10). Here, as seen in FIG. 4, test results demonstrate that NB and OTC drastically lowered the production of TNF-α in vitro at 93.0% and 72.0% respectively while AP lowered production by 44.0% and CBD isolate, as a control, lowered TNF-α by 14.0%. The concentration of CBD isolate was the same as that present in the invention. This evinces the synergistic anti-inflammatory effect of both compositions of the present disclosure and how it is not dependent on only the known anti-inflammatory effects of CBD.

Figure 5:
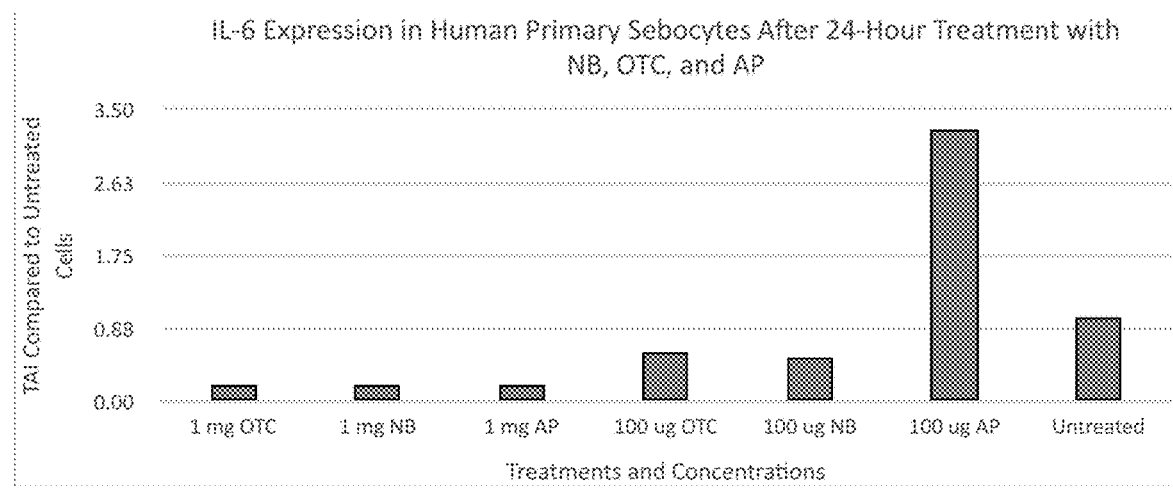
FIG. 5 depicts a table comparing IL-6 expression results.

As already discussed, Interleukin-6 (IL-6) is a well-established marker for inflammation. Reduction of inflammation is beneficial for acne sufferers, as it reduces pain and size of comedones. The results of 1 mg/mL treatment of both compositions of the present disclosure on human primary sebocytes show a large knock-down of this pro-inflammatory cytokine. FIG. 5 demonstrates that OTC and NB reduced IL-6 expression by 80.0% and 82.0% respectively and AP lowered production by 79.0% when tested at 1 mg/mL. The results of treatment with a lower concentration of 100 ug/mL show a reduction in expression of IL-6 with OTC and NB by 41.0% and 46.0% respectively and AP increased expression by 225.0%.

Figure 6:
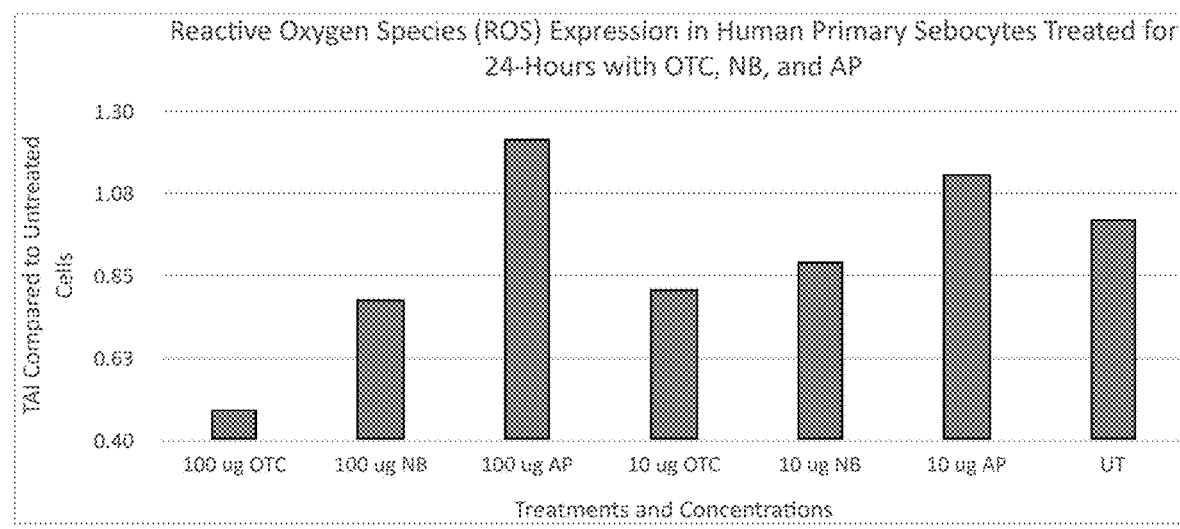
FIG. 6 depicts a table comparing Reactive Oxygen Species expression results.

In acne, sebum produced by sebaceous glands, content changes and reactive oxygen species (ROS) may be released from the impacted damaged follicular walls; at the same time, it is thought that this may be the reason for the progress of the inflammation in the pathogenesis of the disease (Briganti S, Picardo M. Antioxidant activity, lipid peroxidation and skin diseases. What's new? J Eur Acad Dermatol Venereol. 2003; 17(6):663-669). FIG. 6 shows that OTC and NB reduced ROS expression in both concentrations tested, 100.0 ug/mL showed a 51.5% and 21.5% reduction respectively, and 10.0 mg/mL showed an 18.6% and 11.0% reduction while AP increased production in both concentrations tested showing an increase of 22.0% for 100.0 ug/mL and 12.0% for 10.0 ug/mL.

As can be seen, this test suggests that the acne products widely available on the market may promote the acne cycle by increasing pro-inflammatory cytokines such as IL-6. In contrast, both OTC and NB decrease the pro-inflammatory cytokines. It is believed that this will help break the acne cycle long term for individuals suffering from acne.

Figure 7:
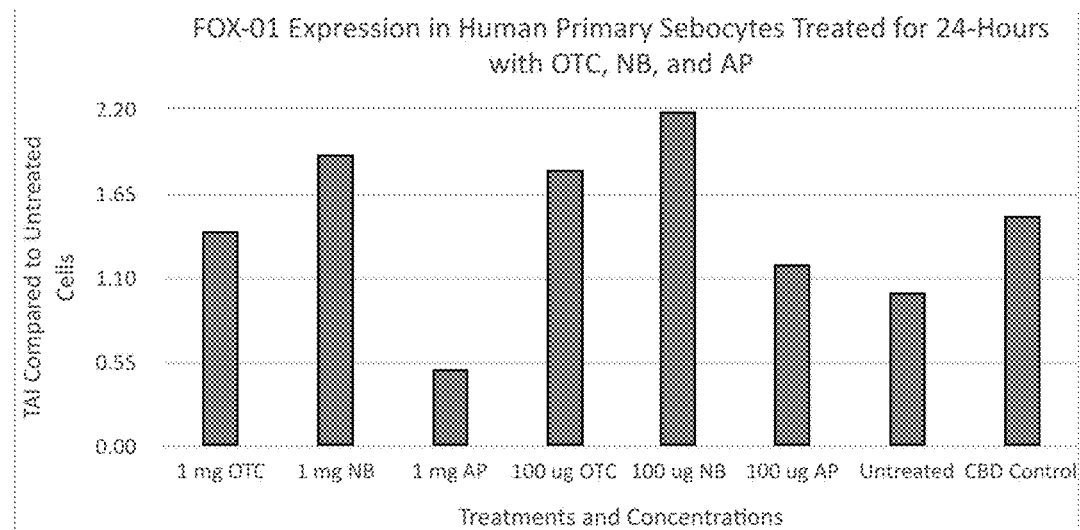
FIG. 7 depicts a table comparing FOX-01 expression results.

Fox-01 is a transcription factor that plays a role in the onset of acne. It is regulated by insulin and the PI3K/Akt pathway to influence the production of sebum. Insulin down-regulates FOX-01 leading to more sebum production by sebocytes which causes comedones. This transcription factor, when up regulated, helps lessen acne pathogenesis. OTC and NB up-regulated FIG. 7 shows that FOX-01 expression in both concentrations tested, 1.0 mg/mL and 100.0 ug/mL while AP decreased expression at 1.0 mg/mL. At 1.0 mg/mL, OTC increased Fox-01 by 40.7% while NB increased it by 90.4% and AP decreased it by 50.2%. At 100 ug/mL, OTC increased Fox-01 by 79.4% while NB increased it by 117.0% and AP increased it by 19.2%. At this concentration, OTC and NB were more effective in increasing Fox-01 expression than CBD isolate alone, which increased expression by 50.8%. This result is unexpected and suggests that there may be a synergic combination within the invention that increases Fox-01 production so effectively.

Figure 8:
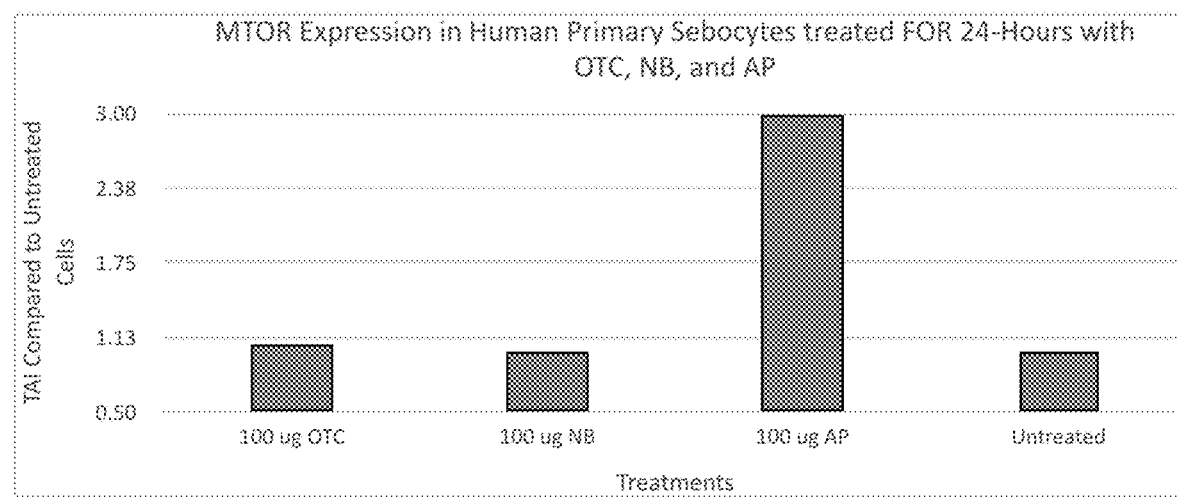
FIG. 8 depicts a table comparing MTOR expression results.

Mechanistic target of rapamycin or mTOR, is a nutrient-sensitive regulator of cellular growth, proliferation, lipid synthesis and protein translation (Brown E J, Albers M W, Shin T B, et al. Nature 1994: 369: 756-758). Much like FOX-01, it is a regulator of the sebum production in sebocytes. When mTOR production is high, sebum production follows along the same trend and increases. FIG. 8 demonstrates that OTC and NB did not interfere with expression at 100 ug/mL, while AP increased expression by 3 times at the same concentration.

Figure 9:
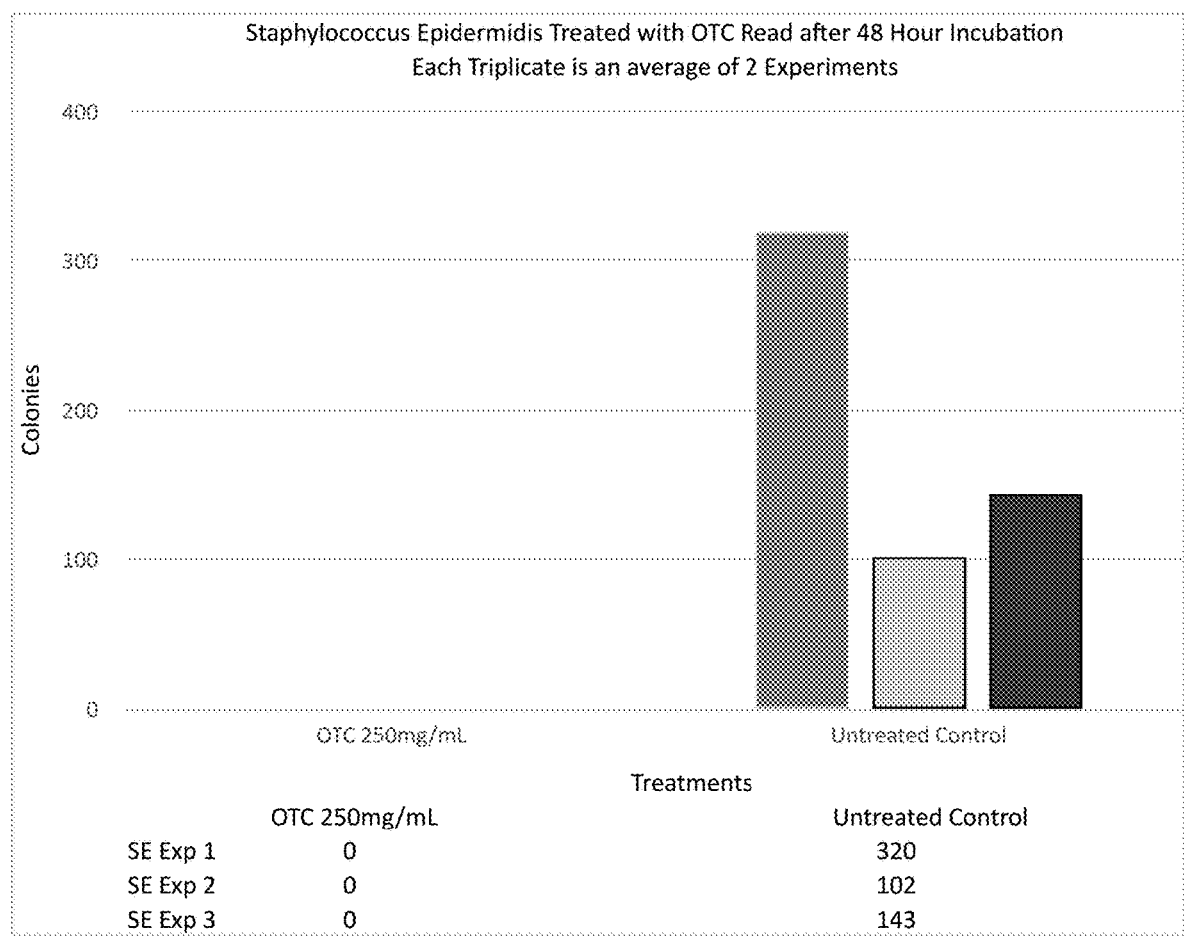
FIG. 9 depicts a table comparing *staphylococcus epidermis* results.

*Staphylococcus epidermidis* is a coagulase-negative, gram-positive cocci bacteria that form clusters. They are the most common coagulase-negative *Staphylococcus* species that live on the human skin. (Hamory B H, Parisi J T, Hutton J P. Staphylococcus epidermidis: a significant nosocomial pathogen. Am J Infect Control. 1987 April; 15(2):59-74). As seen in FIG. 9, *Staphylococcus Epidermidis* is increased on the skin by 70% in acne patients versus control patients and is responsible for biofilm formation which protects this bacteria and *P. acnes* against human innate host defense. It is suggested that a reduction of this bacterium on the skin would decrease the *P. acnes* colonization on the skin as well. OTC effectively kills *S. epidermidis* even after a dilution in water.

REFERENCES

Aslam I, Fleischer A, Feldman S (March 2015). "Emerging drugs for the treatment of acne". Expert Opinion on Emerging Drugs (Review). 20 (1): 91-101.

Bhate K, Williams H C (March 2013). "Epidemiology of acne vulgaris". The British Journal of Dermatology (Review). 168 (3): 474-85.

U.S. Department of Health and Human Services, Office of Public Health and Science, Office on Women's Health. July 2009.

Barnes L E, Levender M M, Fleischer A B, Feldman S R (April 2012). "Quality of life measures for acne patients". Dermatologic Clinics (Review). 30 (2): 293-300, ix.

Stein Gold L F, What's new in acne and inflammation, J Drugs Dermatol. 2013; 12(6):567-s69.

Weiss J S, Messages from molecules: deciphering the code, J Drugs Dermatol. 2013; 12(6):s70-s72.

Bellew S, Thiboutot D, Del Rosso J Q, Pathogenesis of acne vulgaris: what's new, what's interesting and what may be clinically relevant, J Drugs Dermatol. 2011; 10 (6):582-585.

Chapter 4—Exploiting Medicinal Plants as Possible Treatments for Acne Vulgaris Isa Anina Lambrechts, Marco Nuno de Canha and Namrita Lall Pages 117-143

Persson G, Johansson-JănkănpăăE, Gancevicene R, Karadag A S, Bilgili S G, Omer H, Alexeyev O A. No evidence for follicular keratinocyte hyperproliferation in acne lesions as compared to autologous healthy hair follicles. Exp Dermatol. 2018 June; 27(6):668-671. doi: 10.1111/exd.13544. PMID: 29582469.

Irritation Study

A series of experiments were performed in a clinical setting to evaluate skin health parameters including skin irritation, hydration, and smoothness. Human participant's volar forearms were analyzed using.

Histamine is a biologically active chemical compound that is involved in local immune reactions, among other things. When histamine is released into the bloodstream, it triggers an immune response at that location. This immune response, which initially occurs at the cellular level, eventually manifests as visible surface inflammation. The resulting swelling and redness (erythema) can be quantified. For the sake of outputting data in the short term, an irritation study was conducted using histamine to initiate a minor inflammation reaction.

A caliper measures the inflammation site. If the area is circular, the diameter at the greatest point is measured. If oblong, the widest point of length and width are measured. In this experiment, the resulting inflammation was circular for both the control and tested area. Thus, the diameter of the swollen area from the furthest points of redness is measured.

Erythema refers to superficial reddening of the skin due to injury or irritation causing dilatation of the blood capillaries. A specialized piece of skin analytical equipment is capable of measuring this redness on an arbitrary but reputable scale. Courage & Khazaka electronics company has an advanced skin testing device known as the Cutometer® dual MPA 580. One of the respective skin testing probes used in this experiment is the Mexameter® MX 18, which measures erythema and melanin content by light absorption and reflection.

The study participant was subjected to two puncture sites by a 28-gauge, 1.7 mm safety lancet. Two microliters of histamine were applied to the puncture sites and the inflammation response was allowed to proceed for one minute before taking initial measurements. Following the baseline measurement, a small amount of OTC was applied to one of two puncture sites commensurate with what an average consumer would use for their acne. The other was left untreated. Every hour for five consecutive hours the erythema was measured by Mexameter, and the diameter of the site taken by caliper.

Figures 10, 11:
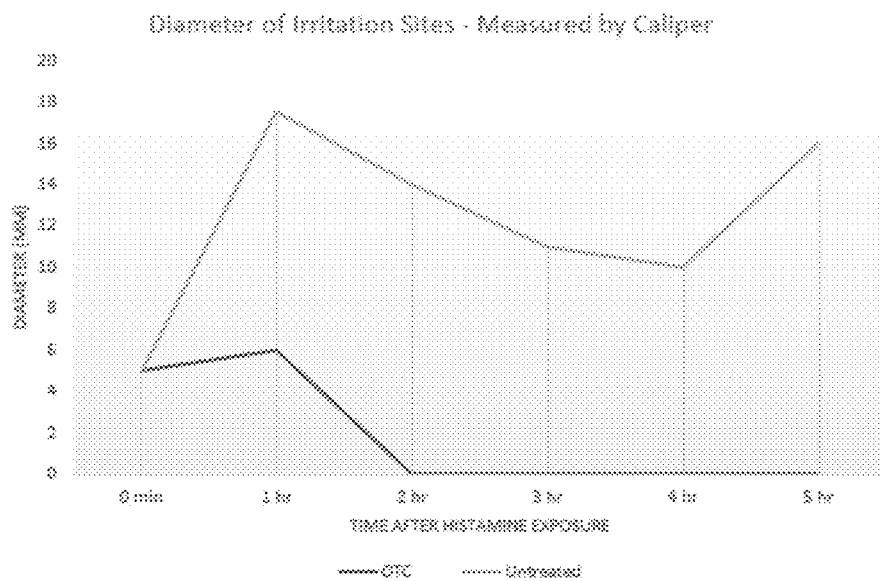
FIG. 10 depicts the results of an irritation study.
FIG. 11 depicts the Mexameter results.

As seen in FIGS. 10 and 11, by two hours post reaction, the OTC treated area had no measurable diameter. The untreated area remained highly red with a measurable irritation site.

The Mexameter data for the untreated control illustrated a sharp increase in erythema, as expected, which occurred over the first hour and then leveled off but maintained a heightened degree. The data was interesting for the OTC treated area. At hour(s) one, two, and three, the measured erythema was significantly lower than the untreated. There was a jump at hour four and a slight decrease from this jump at hour five. The drastic reduction in redness can be attributed to the inflammation reaction which is still occurring in the skin. Although the skin was measurably less red in the OTC treated than the untreated control, the Mexameter measurements are based on more than surface redness.

Over the course of five hours, the untreated area was an average of 58.0% more erythemic than the OTC treated area. Stated differently, the OTC treated area was an average of 36% less erythemic than the untreated area.

Skin Hydration Data

OTC and NB Compared to Three Available Acne Products

Acne products on the market today most often employ either acids, such as salicylic acid, or oxidizers, like benzoyl peroxide, as their formulation driver. Unfortunately for consumers, there are unpleasant side effects related to the use of such chemicals. Skin dryness is one such side effect, which benzoyl peroxide and salicylic acid have both been shown to cause. To determine what effect the OTC and NB compositions of the present disclosure have on moisturization, a simple skin test was performed comparing OTC and NB to three available acne products. Acne Product 1 (AP 1) contained 2.5% benzoyl peroxide, Acne Product 2 (AP 2) contained 10% benzoyl peroxide, and Acne Product 3 (AP 3) contained 2% salicylic acid.

Two trials with five participants were performed. A baseline measurement of skin hydration for each participant was taken. Next, all five products were applied to sectioned areas of the participants forearms. The amount was equivalent to that which one would apply to a small comedone. After ~8 hours, skin hydration measurements were taken again. The results are organized by individual as can be seen in FIGS. 12 and 13 with the average of the results shown in FIG. 14.

For all participants in both trials, OTC and NB improved skin hydration. The results for the AP treatments varied, but generally they either caused a drying effect or only slightly improved hydration.

OTC use resulted in an average of 39.7% more hydrated skin after eight hours. Compared to the best performing AP, OTC had a 2.3× greater hydrating effect.

NB performed even better, with use resulting in an average of 41.5% more hydrated skin after eight hours. Compared to the best performing AP (AP 1), based on our data, NB had a 2.4× greater hydrating effect.

Unlike the AP results, there was not a single instance of a drying effect from either OTC or NB for any of the ten participants. Hydration was improved to some degree in all cases. AP 2 performed the worst with a 7.0% reduction in skin hydration on average. This data suggests that the compositions of the present disclosure will not warrant the unwanted side effect of skin dryness associated with current acne topicals.

Visioscan Results

The Visioscan VC20 Plus is a sophisticated instrument used to characterize skin condition in reference to four parameters: skin smoothness, roughness, scaliness, and wrinkles. It is equipped with a LED UV-A light video camera that allows for high resolution imaging and skin surface analysis. The software is capable of calculating the parameters using the grey level distribution from the camera image it produces.

For purposes of this study, the applicable measurable parameter is skin smoothness. Previous experiments have demonstrated that OTC and NB compositions increase skin hydration. Smoothness is relevant to hydration as hydrated skin is in turn smoother.

Figures 15, 16:
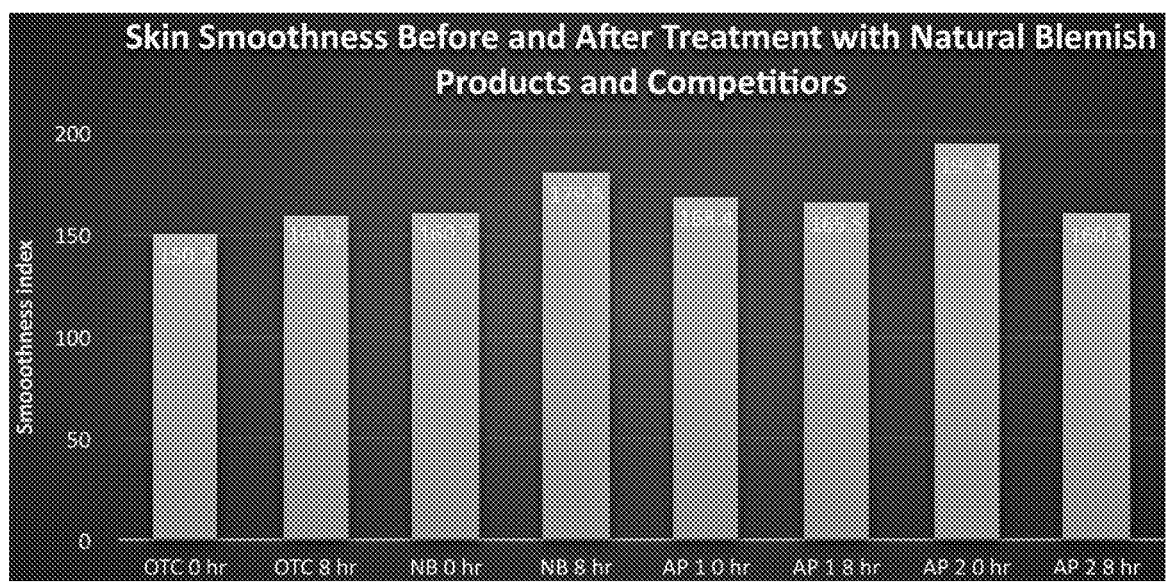
FIG. 15 depicts skin smoothness results.
FIG. 16 skin smoothness results.

Initial photographs were taken and measurements generated for three participants. OTC, NB, AP 1, and AP 2 were applied to the skin at the four respective sections on the forearm. Photos and measurements were taken again at 8 hours post-application. Both OTC and NB compositions demonstrated that they may increase skin smoothness. As seen in FIG. 15, OTC showed a 7.0% increase and NB showed a 12.0% increase. AP 1 and AP 2, which have been shown to dry out the skin, showed a decrease in skin smoothness. AP 1 was more neutral with a 2% decrease, and AP 2 was more drastic with a 17.0% decrease. FIG. 16 shows the average of the results.

This data supports the hypothesis that the OTC and NB compositions are less damaging than those in traditional acne products and may have a rejuvenating effect on the skin.

REFERENCES

Vary J C Jr. Selected Disorders of Skin Appendages—Acne, Alopecia, Hyperhidrosis. Med Clin North Am. 2015 November; 99(6):1195-211. doi: 10.1016/j.mcna.2015.07.003. Epub 2015 Sep. 4. PMID: 26476248.

Barnes L E, Levender M M, Fleischer A B, Feldman S R (April 2012). "Quality of life measures for acne patients". Dermatologic Clinics (Review). 30 (2): 293-300, ix. doi: 10.1016/j.det.2011.11.001. PMID 22284143.

Simonart, T. Immunotherapy for Acne Vulgaris: Current Status and Future Directions. Am J Clin Dermatol 14, 429-435 (2013). https://doi.org/10.1007/s40257-013-0042-8

World Health Organization, Stuart, Marc C, Kouimtzi, Maria & Hill, Suzanne. (2009). WHO model formulary 2008/editors: Marc C. Stuart, Maria Kouimtzi, Suzanne R. Hill. World Health Organization. https://apps.who.int/iris/handle/10665/44053

EXAMPLES

Example 1

A composition of the present disclosure is below:

| Ingredient | % | % range |
| --- | --- | --- |
| Water | q.s. to 100% | 40.00-80.00 |
| Allantoin | 0.30 | 0.05-1.00 |
| Spruce Resin Extract | 15.00 | 5.00-50.00 |
| Xanthan Gum or Magnesium Aluminum Silicate | 0.60 | 0.10-2.00 |
| (Water (and) Sodium PCA (and) Panthenol (and) Glycerin (and) Sodium Hyaluronate (and) Proline (and) Hydroxyproline) | 4.00 | 0.50-10.00 |
| Potassium Cetyl Phosphate | 1.25 | 0.50-10.00 |
| Oleosomes | 5.00 | 1.00-15.00 |
| Full Spectrum Hemp Extract | 1.20 | 0.10-5.00 |
| Cetyl Alcohol | 4.25 | 1.00-10.00 |
| Hemp Seed Oil | 2.00 | 0.10-5.00 |
| Ascorbyl Palmitate | 0.40 | 0.05-2.00 |
| Terpene Blend (alpha bisabolol, limonene, beta-pinene, alpha-pinene, linalool) | 0.50 | 0.01-5.00 |
| Mixed tocopherols | 0.20 | 0.05-2.00 |
| Rosemary extract, mixed tocopherols and ascorbyl palmitate) | 0.20 | 0.01-2.00 |
| Preservative | 0.50 | 0.50 |
| pH adjuster (NaOH solution) | q.s. | 0-2.00 |

Example 2

One composition of the present disclosure, Natural Blemish Light Lotion (NB), is below:

| Ingredient | % | % range |
| --- | --- | --- |
| Water | q.s. | q.s. |
| Spruce Resin Extract | 10.00 | 1.00-40.00 |
| Allantoin/Comfrey | 0.30 | 0.10-5.00 |
| Xanthan Gum | 0.60 | 0.10-5.00 |
| (Water (and) Sodium PCA (and) Panthenol (and) Glycerin (and) Sodium Hyaluronate (and) Proline (and) Hydroxyproline) | 4.00 | 0.10-10.00 |
| Cetyl Alcohol | 4.25 | 1.00-10.00 |
| Potassium Cetyl Phosphate | 1.25 | 0.10-10.00 |
| Cannabis Sativa (Hemp) Seed Oil | 2.00 | 0.10-10.00 |
| Full Spectrum Hemp Extract | 1.49 | 0.01-10.00 |
| CBG (cannabigerol) Isolate | 0.10 | 0.01-5.00 |
| Ascorbyl Palmitate | 0.40 | 0.05-5.00 |
| Bisabolol/Chamomile Extract | 0.20 | 0.01-5.00 |
| Limonene | 0.10 | 0.01-5.00 |
| Pinene | 0.05 | 0.01-5.00 |
| Linalool | 0.10 | 0.01-5.00 |
| Tocopherol | 0.20 | 0.01-5.00 |
| Ascorbyl Palmitate (and) Mixed Tocopherols (and) Rosemary Extract | 0.20 | 0.01-5.00 |
| Preservative | 0.70 | 0.10-2.00 |

Example 3

One composition of the present disclosure, Natural Blemish OTC Lotion (OTC), is below:

| Ingredient | % | % range |
| --- | --- | --- |
| Water | q.s. | q.s. |
| Allantoin/Comfrey | 0.40 | 0.10-5.00 |
| Sodium Hyaluronate | 0.30 | 0.05-5.00 |
| Potassium Cetyl Phosphate | 0.70 | 0.10-10.00 |
| Xanthan Gum | 1.25 | 0.10-5.00 |
| Spruce Resin Extract | 10.00 | 1.00-40.00 |
| Cetyl Alcohol | 4.75 | 1.00-10.00 |
| Carthamus Tinctorius (Safflower) Seed Oil | 2.00 | 0.10-10.00 |
| Nigella Sativa (black cumin) Seed Oil | 0.50 | 0.10-10.00 |
| Caprylic/Capric Triglyceride | 1.00 | 0.10-10.00 |
| Ethyl Linoleate | 0.50 | 0.05-5.00 |
| Full Spectrum Hemp Extract | 1.49 | 0.01-10.00 |
| Salicylic Acid (and) Polydextrose (and) Dextrin (and) Amylopectin (and) Niacinamide | 2.00 | 1.00-5.00 |
| Ascorbyl Palmitate | 0.40 | 0.05-5.00 |
| Bisabolol/ Chamomile Extract | 0.30 | 0.01-5.00 |
| Limonene | 0.10 | 0.01-5.00 |
| Pinene | 0.10 | 0.01-5.00 |
| Linalool | 0.10 | 0.01-5.00 |
| Tocopherol | 0.20 | 0.01-5.00 |
| Ascorbyl Palmitate (and) Mixed Tocopherols (and) Rosemary Extract | 0.20 | 0.01-5.00 |
| Preservative | 0.70 | 0.10-2.00 |

It will be appreciated by those skilled in the art that while the composition for treatment of acne has been described in detail herein, the invention is not necessarily so limited and other examples, embodiments, uses, modifications, and departures from the embodiments, examples, uses, and modifications may be made without departing from the process and all such embodiments are intended to be within the scope and spirit of the appended claims.

What is claimed is:

1. A composition for treating acne in a human in need thereof consisting essentially of therapeutically effective amounts of isolated cannabigerol, isolated cannabidiol, spruce resin, xanthan gum, salicyclic acid, ethyl linoleate and black cumin seed oil.

* * * * *